United States Patent
Halyak

[11] Patent Number: 5,928,133
[45] Date of Patent: Jul. 27, 1999

[54] USER RESPONSIVE SLEEP MONITORING AND AWAKENING DEVICE

[76] Inventor: George Halyak, P.O. Box 2949, Carson City, Nev. 89703

[21] Appl. No.: 09/045,848

[22] Filed: Mar. 23, 1998

Related U.S. Application Data

[63] Continuation of application No. 08/791,809, Jan. 30, 1997, abandoned.

[51] Int. Cl.$^6$ .................................................. A61M 21/00
[52] U.S. Cl. ............................. 600/26; 600/547; 340/575
[58] Field of Search ................................. 600/26, 27, 28, 600/544, 545, 546, 547; 340/575

[56] References Cited

U.S. PATENT DOCUMENTS

| | | |
|---|---|---|
| 4,228,806 | 10/1980 | Lidow . |
| 4,585,011 | 4/1986 | Broughton et al. . |
| 4,725,824 | 2/1988 | Yoshioka . |
| 4,757,825 | 7/1988 | Diamond . |
| 4,776,345 | 10/1988 | Cohen et al. . |
| 4,784,162 | 11/1988 | Ricks et al. . |
| 4,836,219 | 6/1989 | Hobson et al. . |
| 5,101,831 | 4/1992 | Koyama et al. . |
| 5,280,791 | 1/1994 | Lavie . |
| 5,492,113 | 2/1996 | Estes et al. . |

FOREIGN PATENT DOCUMENTS

| | | |
|---|---|---|
| WO 87/03986 | 7/1987 | WIPO . |
| WO 93/02731 | 2/1993 | WIPO . |

*Primary Examiner*—Linda C.M. Dvorak
*Assistant Examiner*—Rosiland Kearney
*Attorney, Agent, or Firm*—Terrance L. Siemens

[57] ABSTRACT

An apparatus and method is disclosed for awakening the user during a preset time interval or bracket at the point when, for all intents and purposes, the user is already awake. At certain periods, discernable by, for instance, measurement of resistance through the body, large $\Delta$'s are observed at certain brief periods, especially close to the beginning and end of REM. At these points, it is possible to wake a person with almost no effort at all, and in many cases, the person will be unaware that they even were sleep.

4 Claims, 2 Drawing Sheets

USER RESPONSIVE SLEEP MONITORING AND AWAKENING DEVICE

REFERENCE TO RELATED APPLICATIONS

This is a continuing application of Ser. No. 08/791,809, filed on Jan. 30, 1997, now abandoned.

FIELD OF THE INVENTION

The present invention relates to an apparatus and method for determining the optimal moments to awaken a user during the sleep cycle. More specifically, it relates to an apparatus and method that monitors various physiological changes that occur during sleep. At moments when the user is virtually awake, the apparatus sets off an audio and/or visual alarm.

BACKGROUND OF THE INVENTION

Sleep difficulties are growing more and more common in the modern world. Few people in the industrialized world wake up "cleanly", that is to say instantly, fully, and comfortably. Hectic schedules, late office hours, meals grabbed at odd times . . . all of these can lead to disturbed or erratic sleep. One of the primary difficulties with unsteady sleep schedules is that waking up can be next to impossible. Alarm clocks have an inherent problem in that they activate at a predetermined time with no physiological input from the subject who is to be woken. If an alarm sounds or activates when the person is in "deep" or delta sleep, wakening will be difficult and the familiar early morning grogginess will be experienced and will persist, possibly for hours. The present invention seeks to address this problem by monitoring the physiological state of the individual and activating an alarm within a predetermined time window when it is sensed that the individual is at an optimal point, that is when they are already virtually awake. The invention plots this physiological data so that it can be used to predict these optimal points over the course of an evening, used for longer term studies in a single individual, or the same long term studies in larger populations.

DISCUSSION OF THE PRIOR ART

Listed hereinafter are patents that are deemed relevant to the present invention:

First is U.S. Pate. No. 4,776,345 issued on Oct. 11, 1988 to Daniel E. Cohen et al. This discloses a method of determining sleep stages. Unlike the present invention, there is no external activation device to wake the subject at a sensed optimal moment.

Next is U.S. Pat. No. 4,228,806 issued on Oct. 21, 1980 to Derek Lidow. This discloses a sleep state inhibited wake-up alarm. This is unlike the present invention in that there is no teaching of the optimal moment for waking the user. Only an inhibiting override that is activated in response to "deep" (or delta) sleep or REM sleep is taught.

Another patent of interest is U.S. Pat. No. 5,101,831 issued to Emi Koyama et al. on Apr. 7, 1992. This discloses a system for discriminating sleep states. Like the Cohen et al. patent above, there are complex mechanisms described to differentiate various stages in the sleep process, but no determination of optimal wake up points is taught.

In International Publication WO 93/02731 for Billon et al. published on Feb. 18, 1993 there is disclosed a programmable biological wake-up device that monitors sleep episodes. This unit senses cardiac rhythms and activates a signal when a desired sleep state is reached. This is unlike the present invention in that there is no teaching of the optimal moment sensing required in the present invention.

International Publication WO 87/03986 for Carl H. Tyrén published on Jul. 2, 1987 discloses a slumber detection method. This is dissimilar from the present invention in that uses a sensitive magnetometer to read EEG signals indicative of falling asleep/losing consciousness.

U.S. Pat. No. 5,492,113 issued on Feb. 20, 1996 to Mark C. Estes et al. discloses an apparatus for sleep apnea treatment. This is clearly dissimilar from the instant invention in that there is no teaching of sensing optimal wake up times.

In U.S. Pat. No. 5,280,791 issued on Jan. 25, 1994 to Peretz Lavie there is disclosed a monitoring system for determining sleep stages. This is unlike the present invention in that there is no determination of an optimal "wake up" point that activates an alarm.

In U.S. Pat. No. 4,836,219 issued on Jun. 6, 1989 to J. Allen Hobson et al. discloses an electronic sleep monitor incorporated in a piece of headgear. As in the patents described above, there is no teaching of any alarm means.

U.S. Pat. No. 4,784,162 issued to Robert D. Ricks et al. on Nov. 15, 1988 discloses a portable physiological data monitoring system. This is clearly dissimilar from the present invention in that, as above, no mention of a wake up alarm is made.

In U.S. Pat. No. 4,585,011 issued on Apr. 29, 1986 to Roger Broughton et al. there is disclosed an eye movement detector. Unlike the present invention, no mention is made of waking up the subject at a sensed optimal time.

U.S. Pat. No. 4,757,825 issued on Jul. 19, 1988 to Donald A. Diamond discloses a cardio-pulmonary activity monitor. This specifically looks for episodes of apnea in the subject, unlike the instant invention, which detects the optimal times for waking the user within a predetermined time period.

Lastly, U.S. Pat. No. 4,725,824 issued on Feb. 16, 1988 to Hideaki Yoshioka discloses a doze prevention system. This records a pattern of eyeblink pulses during a period of time when the user is awake. Deviation from this "alert" state sets off an alarm. There is no teaching of discerning optimal wake up points as seen in the present invention.

None of the above inventions and patents, taken either singly or in combination, is seen to describe the instant invention as claimed.

SUMMARY OF THE INVENTION

The present invention provides an apparatus and method for awakening the user during a preset time interval or bracket at the point when, for all intents and purposes, the user is already awake. At certain periods, discernable by, for instance, measurement of resistance through the body, relatively large $\Delta$'s are observed at certain points of the sleep cycle, especially close to the beginning and end of REM. At these points, it is possible to wake a person with almost no effort at all, and in many cases, the person will be unaware that they even were sleep.

The invention is able to track optimal waking points, which tend to coincide with sleep cycles. These cycles are generally regular and follow a consistent pattern for each individual over the course of a typical night. Thus, the invention not only functions in a manner similar to that of an alarm clock, but also serves to provide the user with data concerning their awakening points, and interruptions thereto, from factors such as diet, exercise, or stress. The individual may program in either a time window or bracket, during which they wish to be awakened, or may simply program in a set time after which the machine would wake them at the first perceived optimal point.

Accordingly, it is a principal object of the invention to provide a user responsive sleep monitoring and awakening device that only activates when the user is at the moment of lightest sleep—virtually, in fact, awake.

It is another object of the invention to provide a user responsive sleep monitoring and awakening device that may be programmed to only activate within a certain time window or after a set time.

Yet another object of the present invention is to provide a user responsive sleep monitoring and awakening device where data concerning the wakeup points of the user may be used to calculate times when the user will be at the point of lightest sleep or virtual wakefulness.

Still yet another object of the present invention is to provide a user responsive sleep monitoring and awakening device that uses physiological information from the user to activate an alarm at an appropriate time.

Still yet another object of the invention is to provide a user responsive sleep monitoring and awakening device that could potentially be used in groups of people, allowing a supervisor or leader to sequentially wake people needed for tasks at the individual's best time for waking.

Still yet another object of the present invention is to provide a user responsive sleep monitoring and awakening device that can be individually programmed for sleep periods less than a full nights sleep, such as naps or 1 or 2 sleep cycles, thus allowing the user to maximize the amount of refreshment and restoration within the shortest period of time.

It is an object of the invention to provide improved elements and arrangements thereof in an apparatus for the purposes described which is inexpensive, dependable, and fully effective in accomplishing its intended purposes.

These and other objects of the present invention will become readily apparent upon further review of the following specifications and drawings.

BRIEF DESCRIPTION OF THE DRAWINGS

A complete understanding of the present invention may be obtained by reference to the accompanying drawings, when taken in conjunction with the detail description thereof and in which.

DESCRIPTION OF THE PREFERRED EMBODIMENT

Figure 1:
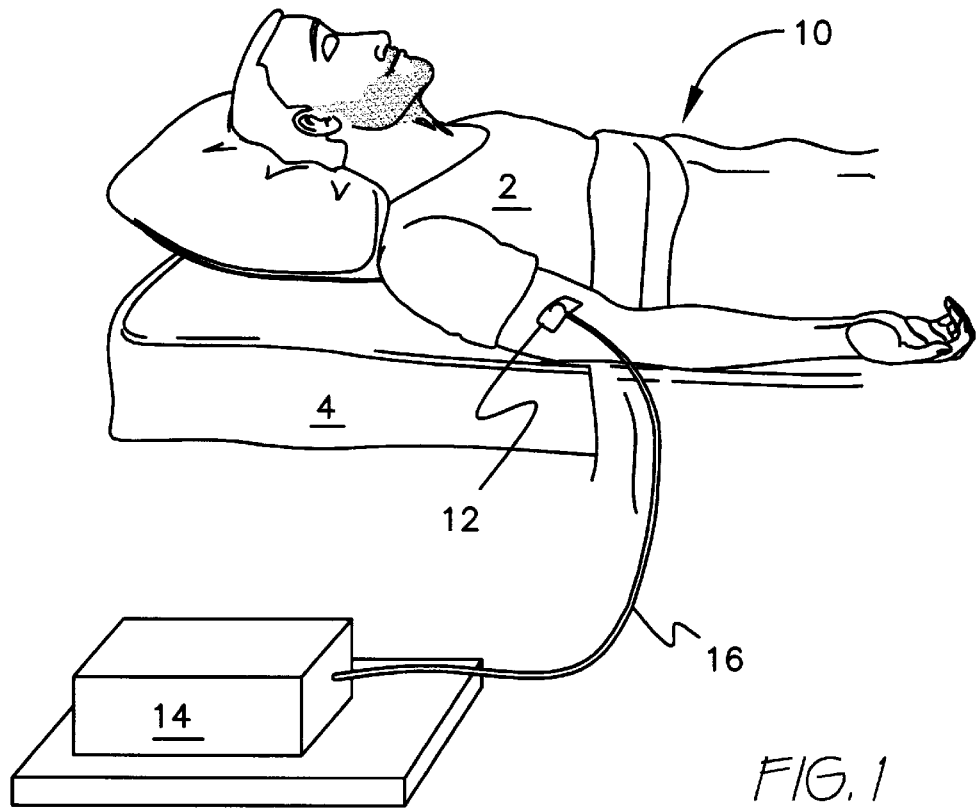
FIG. 1 is an environmental view of the invention

Referring now to FIG. 1 there is seen a person 2 sleeping on a bed 4. Novel apparatus 10 consists, in this described embodiment of a control housing 14, a sensor 12, and a communicating cable 16. In this embodiment, sensor 12 comprises a pair of electrodes, which measure the electrical resistance of the user 2. It should be emphasized a that a wide variety of physiological data could be used to accomplish the purpose of the invention, such as EEGs, heart rate, movement sensors, galvanic skin response, or any other of the common parameters monitored by sleep researchers.

In the embodiment described herein, the electrical resistance of the user 2 is measured in thousands of ohms, hereafter shorted to KΩ. Electrodes measuring resistance are used because this method is relatively non-invasive and easy to attach to oneself before you go to bed. Also note that though the communicating cable 16 is seen in FIG. 1, that it lays entirely within the scope of the invention to eliminate the wiring and use electromagnetic energy of some sort to wirelessly communicate data from sensor 12 to control unit 14.

Figure 2:
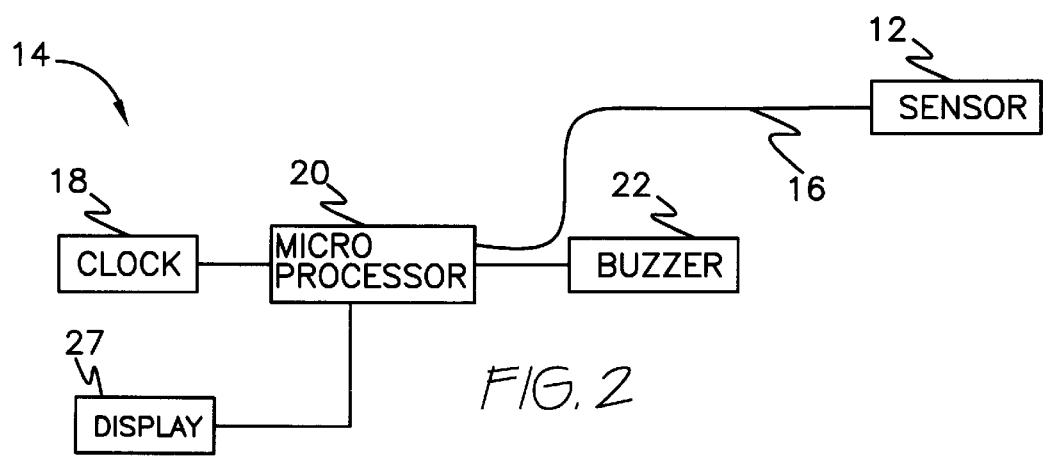
FIG. 2 is a diagrammatic representation of the apparatus seen in FIG. 1.

Turning to FIG. 2, the workings of the control unit 14 will be discussed. Sensor 12 sends data at selected time intervals to microprocessor 20. Microprocessor 20 contains memory that stores and compares this data, as will be discussed in more detail below. Clock 18 is connected to microprocessor and would most preferably be a standard, well known timer chip. Thus microprocessor 20 is able to compare changing values of the data from sensor 12 over time as well as allowing the microprocessor 20 to write the data to memory at specified time intervals. Control unit 14 also contains an alarm or awakening means, depicted here by buzzer 22. Control unit 14 also may include a display 27. Alternatively, control unit 14 may be attachable to a printer, to allow the user to have a permanent record of the data from sensor 12.

Figure 3:
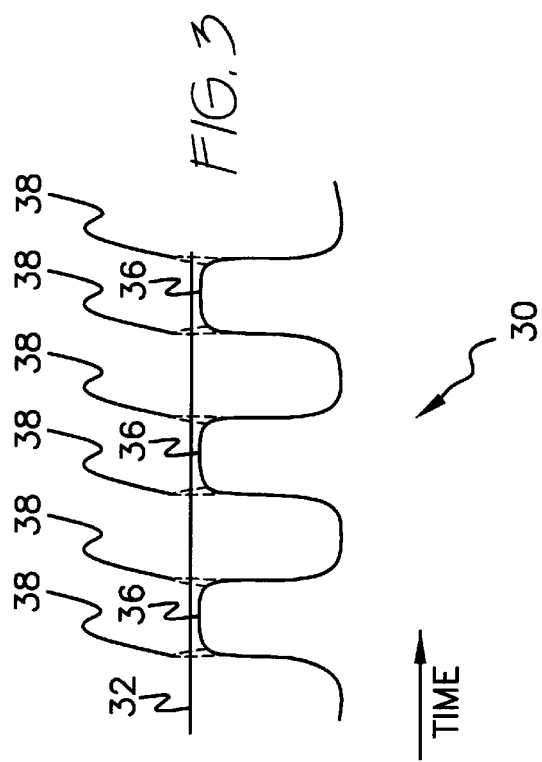
FIG. 3 is a graphical representation of a portion of a sleep cycle graphed against the passage of time.

During sleep, physiological changes occur in the sleeper. These changes are well known and documented. Patents described hereabove, such as Cohen et al. discuss various stages and differentiated types of sleep. Referring to FIG. 3, A rough representation of part of a sleep cycle is indicated at 30. Line 32 indicates the threshold between consciousness and sleep. Indicated at 34 are the periods of deep or "delta" sleep. Indicated at 36 are the periods of lighter or "REM" sleep during which dreaming occurs. At certain points in the sleep cycle, usually at the beginning and end of the REM cycle as is indicated at 38, there are "spikes" of activity. This has been observed as varying degrees of movement to a casual watcher, and during these events the sleeper is, for all intents and purposes, awake. For a given individual, given similar circumstances, sleep positions, and the like, these larger cycles between REM and delta, and the moments of temporary wakefulness, are regular, and can to some degree be predicted. If a person is roused or disturbed at one of these points, in many cases, they will be completely alert and unaware of actually having been asleep. These "spikes" which will be referred to as optimal wake up points in the following further description, can be detected through changes in bodily electrical activity. This is what the present invention does. Unlike a standard alarm clock, which has a preset time for awakening the user, the present invention allows the user to pick a time interval in which to be awakened or to choose a time after which they wish to be awakened. The device will then wait until one of these optimal wake up points is reached and then activate the alarm means.

OPERATION

Referring now to FIG. 1, the sensors 12 are attached to the user at any convenient location. In tests, the top and bottom of the wrist have been used with success. Sensors, 12, in this illustrative embodiment are transcutaneous, electrical nerve stimulation or "TENS" electrodes. Staodyn brand graphite impregnated vinyl electrodes are an example of the type that has been used. Before or after this electrode attachment, the microprocessor 20 in control unit 14 is programmed with various parameters. First, a wake up interval or window is chosen. For example, say between six and seven AM. Then the sample time and interval are set. For example, the microprocessor is instructed to look at the electrical resistance in the body every 3 seconds and review the previous 30 seconds for trend information. The amount of change in the resistance value over that time is noted and it is compared to another value, also predetermined by the user, that is the threshold over which the alarm means is activated. For example, anything greater than a 5% change in the 30 second sample time will activate an alarm. As mentioned above, the resistance values generally range between a few hundred to 200k ohms. Sample times and intervals, along with the threshold value, would be set by the user after a few nights that would serve to calibrate what values are most efficacious for the individual. It has been found, in the case of this illustrative embodiment, that a sharp drop in resistance occurs at the optimal wake up times.

Figure 4:
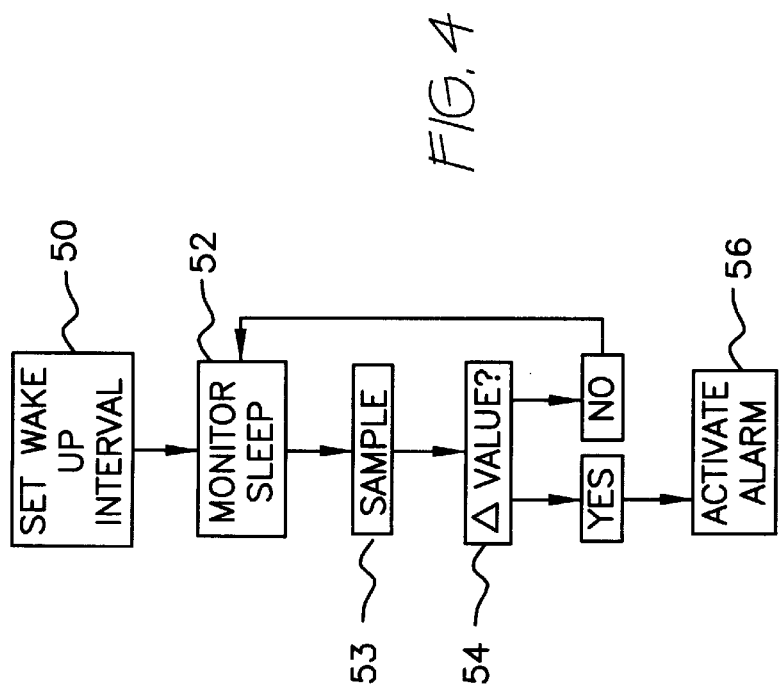
FIG. 4 is a block diagram delineating the steps taken in the operation of the present invention.

Turning to FIG. 4, the operation will be recapped. The interval wake up is indicated at 50. It should be noted that an interval is not absolutely necessary, and that the user could simply indicate a "start" time—say, for example, any optimal wake-up point detected after 6 AM. It also should be noted that a failsafe could be incorporated into the invention, guaranteeing that the alarm will sound at a certain time whether or not an optimal point has been detected. The invention then begins the monitoring process at 52. Samples are taken at preselected intervals over a preselected sampling time interval as seen at 53. These are then compared to a preselected threshold value as indicated at 54. If the threshold value is exceeded, the alarm means is activated as indicated at 56. If it is below the threshold value then the monitoring process continues. Thus, the user will be woken within a certain chosen time at a point where they really are already basically awake. It has been seen in tests that the sleeper can almost immediately go about necessary tasks when awakened at these detected times.

Referring back to FIG. 2, the display means will be discussed. This will not only give a user information concerning their wakeup points and REM periods, but could also be used in groups by a supervisor or leader who needed to awaken someone to perform a task. Take, for example, a group of firemen. If a task needed to be performed, such as a vehicle transported to a certain location, the supervisor of the group could program a central microprocessor (not shown) to wake the next individual who experienced an optimal wake-up point.

Another use of the invention would be to allow a user to take a useful nap (less than or one sleep cycle). This is extremely valuable for people who have to work for long periods of time, such as pilots, truck drivers, military personnel, and the like. Naps, where the individual wakes up cleanly, are desirable when complete sleep restoration is not required to finish a task. As circumstances permit, the individual can target to sleep through one, two, or more sleep cycles. Tests indicate that the greatest amount of restoration occurs during the first sleep cycle. Adding the second sleep cycle, the majority of sleep's restoration has occurred. Thus, shorter periods of rest can be taken and the individual can be confident that they will awaken cleanly and that the benefit of the restoration period will not be ruined by a miserable and/or protracted awakening.

Another use of the invention is to allow an individual to be awakened unobtrusively. This would be useful for those not wishing to bother or to be noticed by others in their environment. Because the individual is so nearly awake at the wakeup moments recognized by the invention, only the slightest of stimuli is necessary to awaken them; a sound at the level of a whisper could be used as opposed to a klaxon, or a gentle touch instead of a shaking.

Having thus described the invention, what is desired to be protected by Letters Patent is presented in the subsequent appended claims.

What is claimed is:

1. Apparatus for awakening a person at an optimal point of wakefulness comprising:

physiological monitoring means for sampling a bodily electrical property, where said bodily electrical property is electrical resistance between two separate points on the person;

measuring means for measuring changes in said electrical resistance over a predetermined time period at predetermined intervals;

comparing means for comparing the changes measured by said measuring means to a predetermined threshold value;

awakening means for awakening the person at the point in time when the changes in said bodily electrical property first exceed said predetermined threshold value.

2. The apparatus according to claim 1, wherein said changes in said measured electrical resistance manifest themselves as rapid spikes at the beginning and the end of the monitored person's REM cycles.

3. A method for monitoring and awakening a person at an optimal point of wakefulness comprising the steps of:

setting a time interval within which the person wishes to be woken;

monitoring a bodily electrical property wherein said bodily electrical activity being monitored is electrical resistance, said monitoring occurring at predetermined intervals over a predetermined sampling period;

measuring changes in said electrical resistance;

comparing the changes in said electrical resistance to a predetermined threshold activating an awakening means when said predetermined threshold is first exceeded within said time interval.

4. The method according to claim 3, wherein said changes in said measured electrical resistance manifest themselves as rapid spikes at the beginning and the end of the monitored person's REM cycles.

* * * * *